(12) United States Patent
Schoville et al.

(10) Patent No.: US 11,497,823 B2
(45) Date of Patent: Nov. 15, 2022

(54) STERILIZATION MANAGEMENT DEVICE AND METHODS FOR OPERATING SAME

(71) Applicant: SURGICAL SAFETY SYSTEMS, LLC, Brighton, MI (US)

(72) Inventors: Fredrick P. Schoville, Brighton, MI (US); Fredrick O. Fortson, Whitmore Lake, MI (US)

(73) Assignee: SURGICAL SAFETY SYSTEMS, LLC, Brighton, MI (US)

( * ) Notice: Subject to any disclaimer, the term of this patent is extended or adjusted under 35 U.S.C. 154(b) by 109 days.

(21) Appl. No.: 16/769,091

(22) PCT Filed: Jul. 24, 2018

(86) PCT No.: PCT/US2018/043420
§ 371 (c)(1),
(2) Date: Jun. 2, 2020

(87) PCT Pub. No.: WO2020/023019
PCT Pub. Date: Jan. 30, 2020

(65) Prior Publication Data
US 2021/0128761 A1 May 6, 2021

(51) Int. Cl.
*A61L 2/07* (2006.01)
*A61L 2/24* (2006.01)
*A61L 2/04* (2006.01)

(52) U.S. Cl.
CPC ...... *A61L 2/07* (2013.01); *A61L 2/24* (2013.01); *A61L 2/04* (2013.01); *A61L 2202/14* (2013.01); *A61L 2202/24* (2013.01)

(58) Field of Classification Search
CPC ..... A61L 2/07; A61L 2/24; A61L 2/04; A61L 2202/14; A61L 2202/24
USPC ........... 422/26; 250/453.114, 454.11, 455.11
See application file for complete search history.

(56) References Cited

U.S. PATENT DOCUMENTS

| 4,865,814 A | 9/1989 | Childress |
| 11,324,845 B1 * | 5/2022 | Ricciardi .................. A61L 2/22 |
| 2009/0304553 A1 | 12/2009 | Gordon |
| 2015/0094914 A1 * | 4/2015 | Abreu ................ B60H 1/00742 701/1 |

(Continued)

FOREIGN PATENT DOCUMENTS

| CN | 206115671 | 4/2017 |
| KR | 20030067464 | 8/2003 |

*Primary Examiner* — Nicole M Ippolito
(74) *Attorney, Agent, or Firm* — Rudy J. Ng; Bozicevic, Field & Francis LLP

(57) ABSTRACT

A method for controlling an environment within a sterilizer device is disclosed. The method includes equipping an interior space of the sterilizer device with an auxiliary device having a temperature sensor, a humidity sensor, a heating element, monitoring temperature within the sterilizer device, receiving, by the sterilization device, information associated with an initiation of a sterilization cycle of the sterilizer device; monitor duration of the sterilization cycle, receiving, by the sterilization device, information associated with an end of a sterilization cycle of the sterilizer device, determining whether a current humidity measurement is above a predefined threshold, and controlling the heating element to an ON operating state when the current humidity measurement is above the predefined threshold.

20 Claims, 4 Drawing Sheets

(56) References Cited

U.S. PATENT DOCUMENTS

2016/0166721 A1\* 6/2016 Brown ...................... A61L 2/20
  422/26
2017/0078400 A1 3/2017 Binder et al.
2019/0321500 A1\* 10/2019 Anderson ................. A61L 2/10

\* cited by examiner

STERILIZATION MANAGEMENT DEVICE AND METHODS FOR OPERATING SAME

TECHNICAL FIELD

This disclosure relates to medical instrument sterilization, and more particularly to systems and methods for monitoring and managing medical instrument sterilization.

BACKGROUND

The statements in this section merely provide background information related to the present disclosure and may not constitute prior art.

Currently, medical instruments are cleaned and placed in a tray for sterilization in a sterilizer, which is sometimes referred to as a converter or an autoclave. The sterilizer runs a sterilization cycle which includes heating the instruments to a predefined temperature set point for a predefined time period. After the cycle is complete, the tray is removed from the sterilizer and placed in a storage area or moved to a medical room for use in a medical procedure. These known sterilizers and known procedures are problematic in that there is no way to ensure that the instruments have reached a certain temperature, reached a certain temperature for a certain duration, or maintain humidity under a threshold after the sterilization cycle.

Therefore, a need exists for monitoring and managing temperature and humidity conditions during the sterilization cycle and for monitoring and managing humidity conditions after the sterilization cycle is complete.

SUMMARY

A method for controlling an environment within a sterilizer device is disclosed. The method includes equipping an interior space of the sterilizer device with an auxiliary device having a temperature sensor, a humidity sensor, a heating element, monitoring temperature within the sterilizer device, receiving, by the sterilization device, information associated with an initiation of a sterilization cycle of the sterilizer device;

monitor duration of the sterilization cycle, receiving, by the sterilization device, information associated with an end of a sterilization cycle of the sterilizer device, determining whether a current humidity measurement is above a predefined threshold, and controlling the heating element to an ON operating state when the current humidity measurement is above the predefined threshold.

This summary is provided merely to introduce certain concepts and not to identify key or essential features of the claimed subject matter.

BRIEF DESCRIPTION OF THE DRAWINGS

One or more embodiments will now be described, by way of example, with reference to the accompanying drawings, in which.

DETAILED DESCRIPTION

Figure 1:
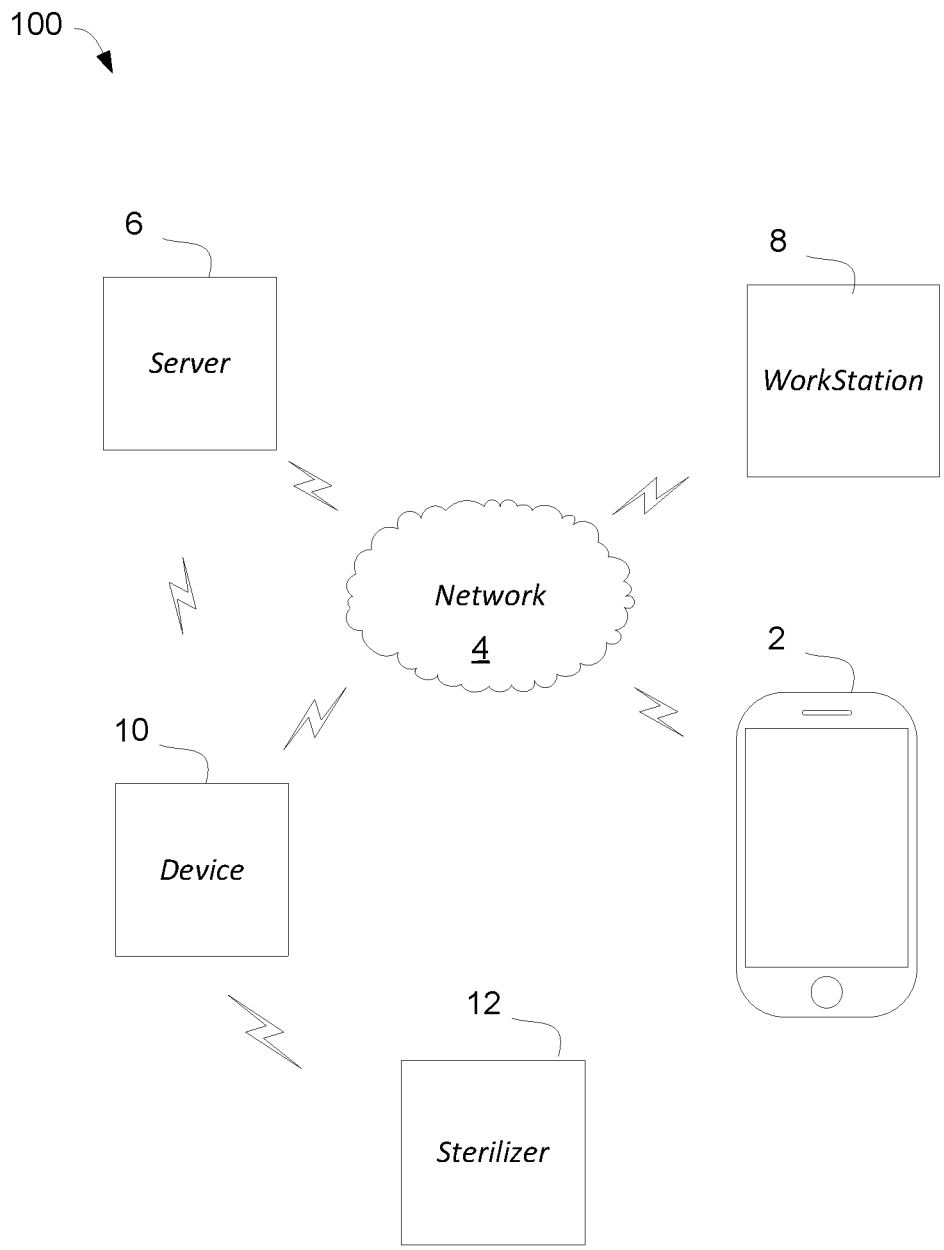
FIG. 1 schematically shows an exemplary sterilization system, in accordance with the present disclosure.

Reference throughout this specification to "one embodiment," "an embodiment," or similar language means that a particular feature, structure, or characteristic described in connection with the embodiment is included in at least one embodiment of the subject matter of the present disclosure. Appearances of the phrases "in one embodiment," "in an embodiment," and similar language throughout this specification may, but do not necessarily, all refer to the same embodiment.

Various embodiments of the present invention will be described in detail with reference to the drawings, where like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

As used in the description herein and throughout the claims, the following terms take the meanings explicitly associated herein, unless the context clearly dictates otherwise: the meaning of "a," "an," and "the" includes plural reference, the meaning of "in" includes "in" and "on." The term "based upon" is not exclusive and allows for being based on additional factors not described, unless the context clearly dictates otherwise. Additionally, in the subject description, the word "exemplary" is used to mean serving as an example, instance or illustration. Any embodiment or design described herein as "exemplary" is not necessarily to be construed as preferred or advantageous over other embodiments or designs. Rather, use of the word exemplary is intended to present concepts in a concrete manner.

Referring now to the drawings, wherein the depictions are for the purpose of illustrating certain exemplary embodiments only and not for the purpose of limiting the same, FIG. 1 schematically shows an exemplary tissue analysis system 100 that may help implement the methodologies of the present disclosure. The system 100 includes a workstation computer 8, a server system 6, a network 4, and a mobile device 2. As shown in FIG. 1, the sterilization device 10 may be communicatively connected to one or more computing devices including a server 6, a workstation computer 8, and/or a mobile device 2. The sterilization device 10 may be indirectly communicatively connected to the one or more computing devices via the network 4 or directly, communicatively connected via wireless protocol. Any one or more of the one or more computing devices may be communicatively connected to one another. For example, the server system 6 may be directly communicatively connected to the workstation computer 8 and the mobile device 2. The mobile device 2 may be physically connected to the network 4 or the workstation computer 8 during selected periods of operation without departing from the teachings herein. Components of the system 100 are shown in FIG. 1 as single elements. Such illustration is for ease of description and it should be recognized that the system 100 may include multiple additional mobile and computing devices.

The network 4 may be any suitable series of points or nodes interconnected by communication paths such as a local wired and/or wireless network. The network 4 may be interconnected with other networks and contain sub networks network such as, for example, a publicly accessible distributed network like the Internet or other telecommunications networks (e.g., intranets, virtual nets, overlay networks and the like). The network 4 may facilitates the exchange of data between and among the sterilization device 10, the mobile device 2, the workstation computer 8, and the server system 6, as requested.

The workstation computer 8 and the server system 6 may each be: various embodiments of a computer including high-speed microcomputers, minicomputers, mainframes, and/or data storage devices. The server system 6 preferably executes database functions including storing and maintaining a database and processes requests from the sterilization device 10, the mobile device 2 and/or the workstation computer 8 to extract data from, or update, a database as described herein below. The server 6 may additionally provide processing functions for the sterilization device 10, the mobile device 2 and the workstation computer 8 as will become apparent to those skilled in the art upon a careful reading of the teachings herein.

In addition, one or more of the sterilization device 10, the mobile device 2 and the workstation computer 8 may include one or more applications that the user may operate. Operation may include downloading, installing, turning on, unlocking, activating, or otherwise using the application. The application may comprise at least one of an algorithm, software, computer code, and/or the like, for example, mobile application software. In the alternative, the application may be a website accessible through the world wide web, for example.

The sterilizer 12, which is sometimes referred to as a converter or an autoclave is a device configured to sterilize medical instruments of one or more of microbial life, including transmissible agents, e.g., fungi, bacteria, viruses, or spore forms, which may be present on a surface, or contained in a fluid, or in medication, or in a compound such as biological culture media. Embodiments of the sterilizer 12 may apply heat, chemicals, irradiation, high pressure, or filtration or combinations thereof. In one embodiment, the sterilizer is configured to use steam heated to a predefined temperature or a selected temperature. To achieve a degree of sterility, a holding time at the predefined temperature is generally executed. Post-sterilization, the sterilizer 12 may operate to control temperature and humidity conditions therein. In one embodiment, the sterilizer includes a heating element and/or a fan.

Figure 2:
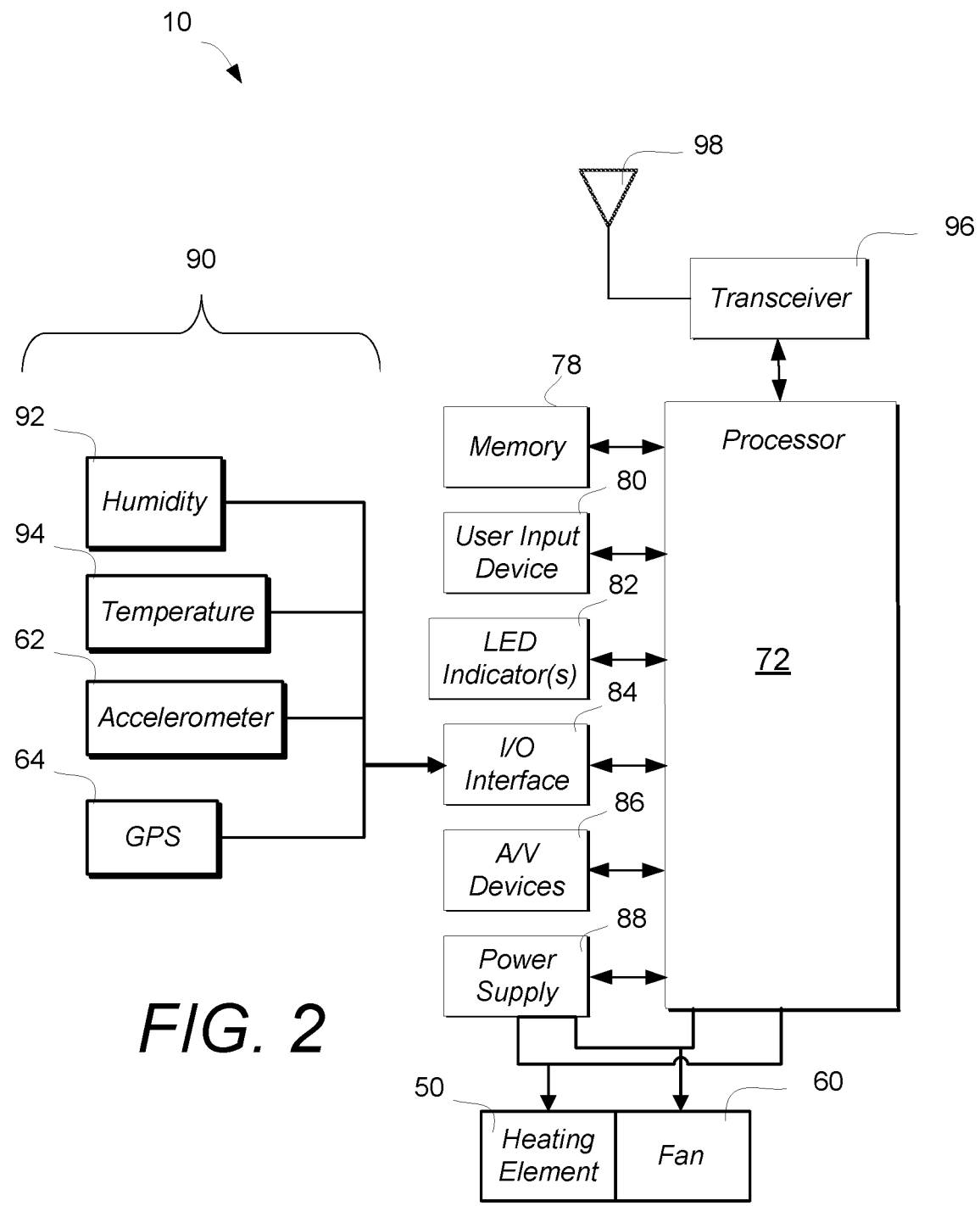
FIG. 2 schematically shows an exemplary sterilization device, in accordance with the present disclosure.

FIG. 2 schematically shows an exemplary embodiment of the sterilization device 10. As shown in FIG. 2, the device 10 includes a processor module 72. The device 10 may additionally include any digital and/or analog circuit elements, comprising discrete and/or solid state components, suitable for use with the embodiments disclosed herein. One skilled in the art will recognize upon a careful reading of the teachings herein that a radio processor may be included in another embodiment of the device 10. In one embodiment, a communication adapter and/or transceiver is utilized for wireless communication over one or more wireless communications channels. Although various components are shown as separate components, such an illustration is for ease of description and it should be recognized that the functions performed by the various components may be combined on one or more components.

The processor module 72 may be configured to execute various computer programs (e.g., software, firmware, or other code) such as application programs and system programs to provide computing and processing operations for the device 10. In various embodiments, processor module 72 may be implemented as a host central processing unit ("CPU") using any suitable processor or logic device, such as a general purpose processor, or other processing device in alternative embodiments configured to provide processing or computing resources to device 10. For example, processor module 72 may be responsible for executing various computer programs such as application programs and system programs to provide computing and processing operations for device 10. The application software may provide a graphical user interface ("GUI") to communicate information between device 10 and a user. The computer programs may be stored as firmware on a memory associated with processor 72, may be loaded by a manufacturer during a process of manufacturing device 10, and may be updated from time to time with new versions or software updates via wired or wireless communication.

System programs assist in the running of a computer system. System programs may be directly responsible for controlling, integrating, and managing the individual hardware components of the computer system. Examples of system programs may include, for example, an operating system, a kernel, device drivers, programming tools, utility programs, software libraries, an application programming interface ("API"), a GUI, and so forth.

The memory module 78 is preferably coupled to the processor module 72. In various embodiments, the memory module 78 may be configured to store one or more computer programs to be executed by the processor module 72. The memory module 78 may be implemented using any machine-readable or computer-readable media capable of storing data such as volatile memory or non-volatile memory, removable or non-removable memory, erasable or non-erasable memory, writeable or re-writeable memory, and so forth. Although the memory module 78 is shown as being separate from the processor module 72 for purposes of illustration, in various embodiments some portion or the entire memory module 78 may be included on the same integrated circuit as the processor module 72. Alternatively, some portion or the entire memory module 78 may be disposed on an integrated circuit or other medium (e.g., solid state drive) external to the integrated circuit of the processor module 72.

A user input device 80 may be coupled to the processor module 72. The user input device 80 may include, for example, an alphanumeric, numeric key layout and an integrated number dial pad. The device 10 also may include various keys, buttons, and switches such as, for example, input keys, preset and programmable hot keys, left and right action buttons, a navigation button such as a multidirectional navigation button, power/end buttons, preset and programmable shortcut buttons, a volume rocker switch, a ringer on/off switch having a vibrate mode, a keypad and so forth. In one embodiment, the device 10 simply includes an ON and an OFF button, the other controls being activated through a wirelessly connected computing device, such as the workstation 8.

The processor module 72 may be coupled to one or more light-emitting diodes (LEDs) 82. In one embodiment, a first LED of the one or more LEDs is used to indicate a first status. In one embodiment, a second LED is used to indicate a second status. In one embodiment, the first status is associated with a green color and the second status is associated with a red color. In one embodiment, a third LED may be used to associate with a third status, e.g., a yellow color. Statuses may predefined as 'sterile'; 'not sterile', or 'in operation.'

An I/O interface 84 is preferably coupled to the processor module 72. The I/O interface 84 may include one or more I/O devices such as a serial connection port, an infrared port, Blue Tooth Low Energy (BLE), Mesh Networks, wireless capability, and/or integrated 802.11x (WiFi) wireless capability, to enable wired (e.g., USB cable) and/or wireless connection to a local or networked computer system, such as the workstation 8, and/or the server 6.

In one embodiment, the device 10 includes an audio/video ("A/V") module 86 coupled to the processor module 72 for communicatively connecting and communicating therebetween to various audio/video devices. The A/V module 86 may be configured to support A/V capability of the device 10 including components such as, a microphone, one or more speakers, an audio port to connect an audio headset, an audio coder/decoder (codec), an audio player, a video codec, a video player, and so forth. The A/V input module 86 may include an imaging module configured to capture digital images. The imagining module may include an optical sensor, e.g., a charged coupled device (CCD) or a complementary metal-oxide semiconductor (CMOS) optical sensor to facilitate camera functions, such as recording photographs and video clips. The image frames may be processed by the memory 78 or displayed on the display 82.

A power supply 88 configured to supply and manage power to components of device 10 is preferably coupled to the processor module 72. In various exemplary embodiments, the power supply 88 may be implemented by a rechargeable battery, such as a removable and rechargeable lithium ion battery to provide direct current ("DC") power, and/or an alternating current ("AC") adapter to draw power from a standard AC main power supply.

The device 10 may include one or more transceivers 96 coupled to the processor 72 and an antenna 98, each transceiver may be configured to communicate using different types of protocol, e.g., Bluetooth®, Near Field Communications, Mesh network, etc., communication ranges, operating power requirements, RF sub-bands, information types (e.g., voice or data), use scenarios, applications, and so forth. For example, the transceiver 96 may include a Wi-Fi transceiver and a cellular or WAN transceiver configured to operate simultaneously. In various embodiments, the transceiver is alternated for a transmitter and/or receiver.

In one embodiment, the device 10 includes a plurality of sensors 90. The sensors may be directly coupled to the processor 72 or connected through one or more other modules including, e.g., the I/O interface, such as shown in FIG. 2. In one embodiment, a humidity sensor 92 is included. In one embodiment, a temperature sensor 94 is included. In one embodiment, the temperature sensor, is an infrared reader. In one embodiment, an accelerometer 62 is included. The accelerometer 62 may be a three-axis accelerometer.

In one embodiment, the sterilizer device 10 includes a heating element 50. The heating element 50 is connected to the power supply and a logic controller such as the processor 72. The heating element 50 is configured for selective operation and may be controlled based upon temperature and/or humidity readings from the device 10. In one embodiment, the heating element 50 may include one or more operating states such as an ON operating state, an OFF operating state, and/or a plurality of power level operating states.

In one embodiment, the sterilizer 10 includes a fan 60. The fan may be coupled to the heating element 50. The fan 60 is connected to the power supply 88 and a logic controller such as the processor 72. The fan 60 is configured for selective operation and may be controlled based upon temperature and/or humidity readings from the device 10. In one embodiment, the fan 60 may include one or more operating states such as an ON operating state, an OFF operating state, and/or a plurality of power level operating states.

Figure 3:
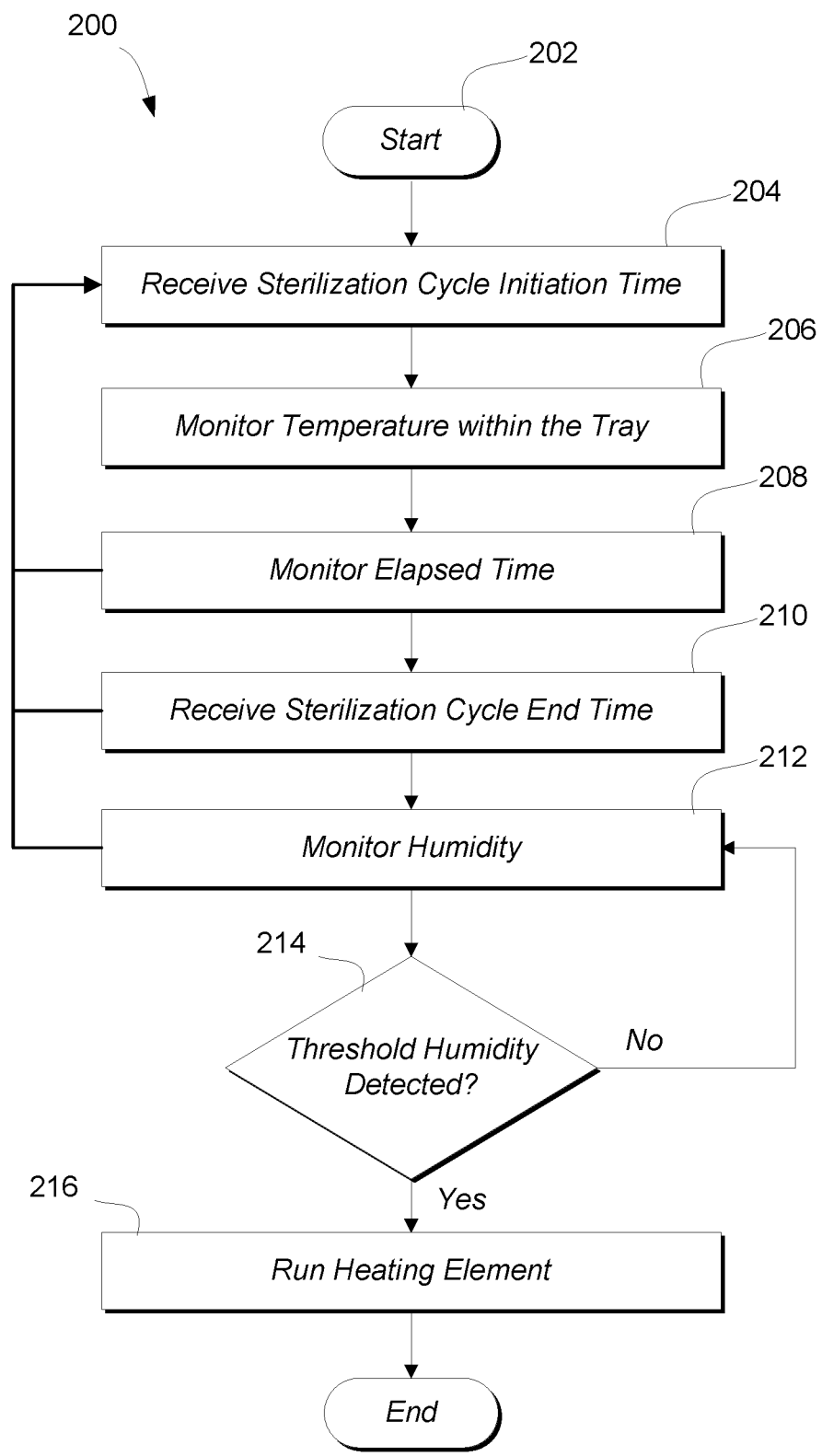
FIG. 3 is a logical flow diagram illustrating one embodiment of the generalized method for controlling a sterilizer device, in accordance with the present disclosure.

Referring now to FIG. 3, one embodiment of a generalized method 200 for managing sterilization status in a contained space is illustrated. The method 200 may be utilized in conjunction with the system 100 and the device 10. In one implementation, the device 10 is positioned with a contained space such as within a medical or surgical tray. The device 10 is capable of selectively communicating with one or more computing devices within the exemplary system 100 as will be discussed in more detail below.

The method 200 may be initialized manually or automatically in accordance with other executing processes. In one embodiment, the method 200 is initialized by simply turning the device 10 to an ON operating state. In one embodiment, the method 200 is initialized by receiving instructions from a computer program to start. For example, in a sterilization tray, a sterilization cycle may be initiated to condition the environment within the tray in order to sterilize medical instruments therein. The sterilization cycle may include sending an initiation instruction to the device 10 to start 202.

At step 204, the device 10 receives information from the sterilizer 12 that a sterilization cycle as begun. The information may be transmission of an ON operating status of the tray associated with the device 10, or the ON operating status of the sterilizer 12 as a whole.

At step 206, the device 10 begins monitoring temperature within a tray within the sterilizer 12. The monitored temperature may be stored by the device 10 for subsequent transmission and/or transmitted for storage. Temperature readings may be made at a predefined time period, e.g., every second. In one embodiment, temperature readings are associated with a time that the measurement occurred. The time may be normalized to the initiation time of the sterilization cycle or a time of day.

At step 208, the device 10 monitors elapsed time. Elapsed time is monitored to determine a time duration of the sterilization cycle.

At step 210, the device 10 receives information associated with the sterilization cycle end. The information may be transmission of an ON operating status of the tray associated with the device 10, or the ON operating status the sterilizer 12 as a whole.

At step 212, the device 10 determines a maximum temperature reading that occurred during the sterilization cycle and an associated time when the maximum temperature reading was made. In one embodiment, one of the computing devices determines the maximum temperature reading and the associated time when the maximum temperature reading was made, subsequent to receiving all of the temperature reading information from the device 10.

At step 216, the device 10 signals the sterilizer 12 to run the heating element 50 and/or the fan 60.

Figure 4:
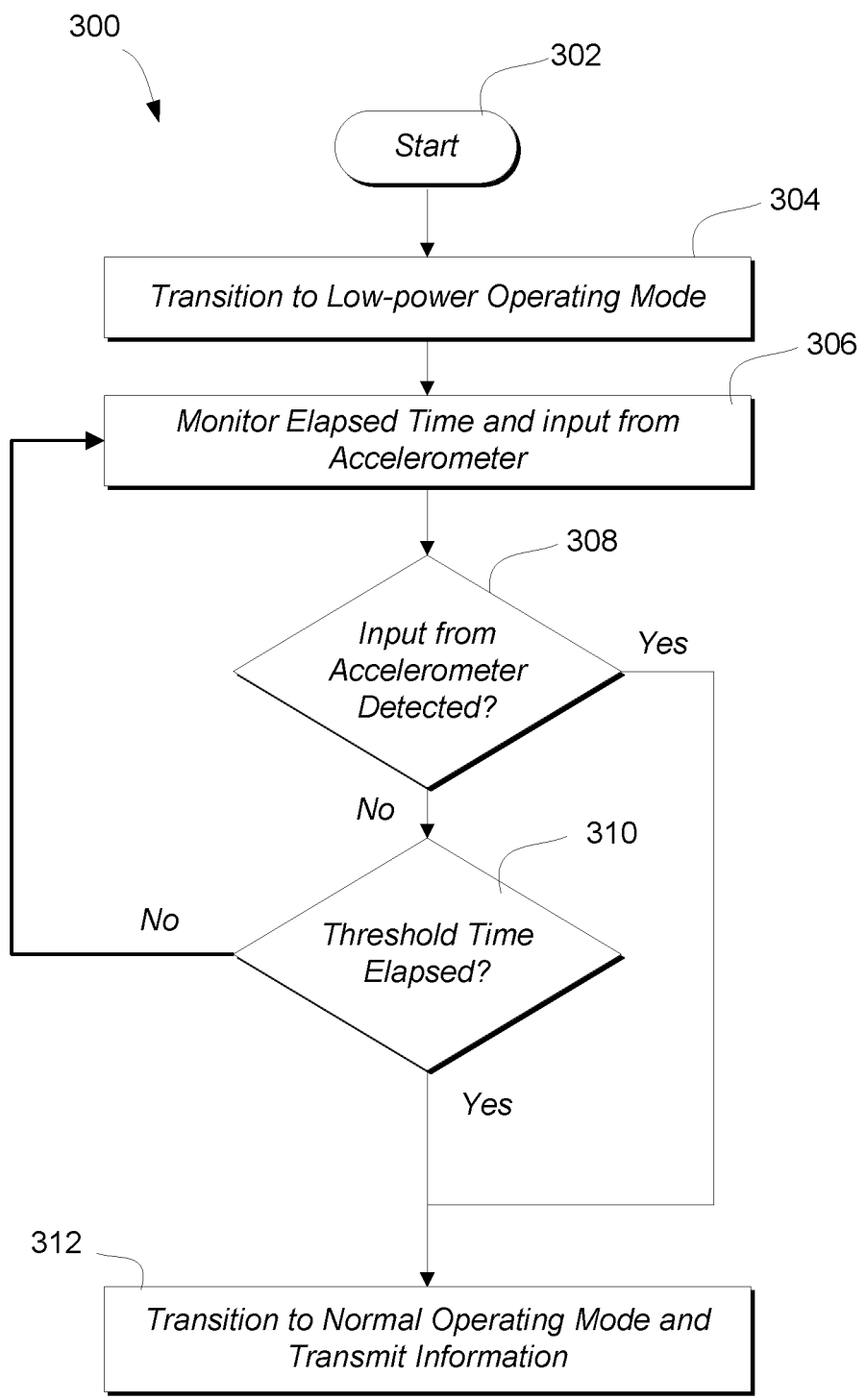
FIG. 4 is another logical flow diagram illustrating one embodiment of the generalized method for controlling a sterilizer device, in accordance with the present disclosure.

Referring now to FIG. 4, one embodiment of a generalized method 300 for transitioning between a LOW-POWER operating state and a NORMAL (or ON) operating state is illustrated. The method 300 may be utilized in conjunction with the system 100, the device 10, and the method 200. In one implementation, the device 10 is positioned with a contained space such as within a medical or surgical tray. The device 10 is capable of selectively communicating with one or more computing devices within the exemplary system 100 as will be discussed in more detail below.

The method 300 may be initialized manually or automatically in accordance with other executing processes. In one embodiment, the method 300 is initialized 302 by simply turning the device 10 to an ON operating state. In one embodiment, the method 300 is initialized by receiving instructions from a computer program to start. In one embodiment, one or more criteria may be used to initiate the method 300 including, e.g., input not received from an accelerometer 62 for a predefined time period. Input not received from the accelerometer 62 generally indicates no movement of the device 10.

In one embodiment, upon initiation 302 of the method 300, the device 10 transitions to a LOW-POWER operating mode. The LOW-POWER operating mode includes no transmitting of temperature or humidity data, i.e., no wireless broadcast of information. In one embodiment, the LOW-POWER operating mode includes transitioning the heating element 50 and the fan 60 to an OFF operating state and preventing transition of the heating element 50 and the fan 60 to an ON operating state.

During the LOW-POWER operating mode, illustrated as step 306, the device 10 monitors elapsed time and input from the accelerometer 62. The accelerometer 62 is configured to emit an electrical output when moved. In one embodiment of the accelerometer 62, electrical output may be made from three prongs, each associated with an axis of movement. Movement of the accelerometer 62 along one or more of the axis causes electrical output out of one or more of the prongs or electrical contact points. When the accelerometer 62 is not moving, no electrical output is made and therefore there is no input received. Elapsed time is simply the time elapsed since transitioning into the LOW-POWER operating mode.

At step 308, the device 10 determines whether input from the accelerometer 62 has been detected. In one embodiment, the processor 72 includes functionality that is configured to act upon receiving an electrical output. For example, the processor 72 does not need to ping the accelerometer 62 to determine whether there has been movement, the processor 72 simply waits until an electrical response is received, the receipt of which indicates that there is movement. In one embodiment, a threshold electrical response is set. A voltage, for example, less than the threshold is not enough to indicate movement, while a voltage greater than the threshold is enough to indicate movement. If movement is inferred from the electrical response from the accelerometer 62, the device 10 transitions to the normal operating mode 312.

In one embodiment, the device 10 is configured to periodically transition from the LOW-POWER operating mode to the normal operating mode. In this way, power is conserved by the device 10, thereby extending potential monitoring and reporting time of the device 10. In one embodiment, the device 10 monitors elapsed time once the device 10 enters the LOW-POWER operating mode. In this way, the device 10 may transition out of the LOW-POWER operating mode periodically, and thereby may periodically transmit information, e.g., device status, temperature information, humidity information, etc., and then transition back to the LOW-POWER operating mode. In one embodiment, the periodic cycle is established by setting a threshold elapsed time. The device 10 may then transition to the NORMAL operating mode when the threshold time has elapsed 310.

In one embodiment, the device 10 may be configured to determine a location. The device 10 may utilize one or more position determination techniques including, for example, GPS techniques, Cell Global Identity ("CGI") techniques, CGI including timing advance ("TA") techniques, Enhanced Forward Link Trilateration ("EFLT") techniques, Time Difference of Arrival ("TDOA") techniques, Angle of Arrival ("AOA") techniques, Advanced Forward Link Trilateration ("AFTL") techniques, Observed Time Difference of Arrival ("OTDOA"), Enhanced Observed Time Difference ("EOTD") techniques, Assisted GPS ("AGPS") techniques, hybrid techniques (e.g., GPS/CGI, AGPS/CGI, GPS/AFTL or AGPS/AFTL for CDMA networks, GPS/EOTD or AGPS/EOTD for GSM/GPRS networks, GPS/OTDOA or AGPS/OTDOA for UMTS networks), etc. Position determination techniques may be based on signals from one or more nearby cellular towers, one or more Wi-Fi access points, BLE, and or Mesh Network (in which position is determined at least in part by collecting addresses of nearby wireless access points and comparing the addresses to a pre-stored database which associates addresses to geographic position), or other techniques. The device 10 can communicate location information upon determination, at various intervals, upon occurrence of trigger events, upon requests, or the like. For example, the device 10 can retrieve location information at the request of one or more network nodes and/or devices. By way of another example, the server 5 can use network elements to determine the location of the device 10 as described herein above.

In various embodiments, the device 10 may include dedicated hardware circuits or structures, or a combination of dedicated hardware and associated software, to support position determination. For example, the transceiver 96 and the antenna 98 may include GPS receiver or transceiver hardware and one or more associated antennas coupled to the processor 72 to support position determination.

In one embodiment, supplemental devices in proximity to the device, such as a mobile device having position determination capabilities may be used to associate position of the mobile device to the device 10 that is proximately located. In one embodiment, location of the mobile device is associated with the device 10 by use of a software application being executed on the mobile device. The mobile device user may request a position association through the software application. The mobile device determines the location and transmits to the device or the server 6 with appropriate association information.

The schematic flow chart diagrams included herein are generally set forth as logical flow chart diagrams. As such, the depicted order and labeled steps are indicative of one embodiment of the presented process. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the process. For example, an arrow may indicate a waiting or monitoring period of unspecified duration between enumerated steps of the depicted process. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

Additionally, the order in which a particular method occurs may or may not strictly adhere to the order of the corresponding steps shown. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures. For example, steps 206 and 208, and 308 and 310 may be executed concurrently in some embodiments.

Additionally, examples in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

As will be appreciated by one skilled in the art, aspects of the present invention may be embodied as a system, method, and/or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product embodied in one or more computer readable medium(s) having program code embodied thereon.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of computer readable program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of computer readable program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the computer readable program code may be stored and/or propagated on in one or more computer readable medium(s).

The computer readable medium may be a tangible computer readable storage medium storing the computer readable program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable medium may include but are not limited to a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store computer readable program code for use by and/or in connection with an instruction execution system, apparatus, or device.

The computer readable medium may also be a computer readable signal medium. A computer readable signal medium may include a propagated data signal with computer readable program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport computer readable program code for use by or in connection with an instruction execution system, apparatus, or device. Computer readable program code embodied on a computer readable signal medium may be transmitted using any appropriate medium, including but not limited to wireless, wireline, optical fiber cable, Radio Frequency (RF), or the like, or any suitable combination of the foregoing In one embodiment, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

Computer readable program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The computer readable program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

While the foregoing disclosure discusses illustrative embodiments, it should be noted that various changes and modifications could be made herein without departing from the scope of the described embodiments as defined by the appended claims. Accordingly, the described embodiments are intended to embrace all such alterations, modifications and variations that fall within scope of the appended claims. Furthermore, although elements of the described embodiments may be described or claimed in the singular, the plural is contemplated unless limitation to the singular is explicitly stated. Additionally, all or a portion of any embodiment may be utilized with all or a portion of any other embodiments, unless stated otherwise.

The invention claimed is:

1. Method for controlling an environment within a sterilizer device, the method comprising:
equipping an interior space of the sterilizer device with an auxiliary device having a temperature sensor, a humidity sensor, a heating element, and a wireless transceiver configured to communicate sensor readings;
monitoring temperature within the sterilizer device;
receiving, by the sterilization device, information associated with an initiation of a sterilization cycle of the sterilizer device;
monitoring duration of the sterilization cycle;
receiving, by the sterilization device, information associated with an end of a sterilization cycle of the sterilizer device;
determining whether a current humidity measurement is greater than a predefined threshold; and
controlling the heating element to an ON operating state when the current humidity measurement is greater than the predefined threshold.

2. The method of claim 1, wherein the auxiliary device further comprises an accelerometer and wherein the method further comprises:
monitoring output from the accelerometer;
monitoring elapsed time without receiving an electrical response from the accelerometer based upon the monitored output; and
transitioning the auxiliary device to a LOW-POWER operating state when the monitored elapsed time is greater than a second predefined threshold.

3. The method of claim 2, further comprising:
transitioning the auxiliary device to a NORMAL operating state when output is monitored from the accelerometer;
transmitting the duration of the sterilization cycle and information associated with the monitored temperature and the current humidity measurements to a server subsequent to transitioning to the NORMAL operating state.

4. The method of claim 2, wherein the LOW-POWER operating state comprises transitioning the wireless transceiver of the auxiliary device to an OFF operating state.

5. The method of claim 1, further comprising:
determining a start time of the sterilization cycle based upon the monitored temperature within the sterilizer device, wherein the start time corresponds to a time when a discrete temperature change occurs greater than a second predefined threshold;
determining an end time of the sterilization cycle based upon the monitored temperature within the sterilizer device, wherein the end time corresponds to a time when monitored temperature change begins to decrease at a predefined rate; and
determining a time duration of the sterilization cycle based upon the start time and the end time.

6. The method of claim 5, further comprising:
determining a maximum temperature reading that occurred.

7. The method of claim 1, wherein the determining whether a current humidity measurement is above a predefined threshold is executed subsequent to the sterilization cycle.

8. The method of claim 1, wherein the auxiliary device further comprises a fan and wherein the method further comprises controlling a fan to an ON operating state when the current humidity measurement is above the predefined threshold.

9. A non-transitory computer readable storage medium storing one or more programs, the one or more programs comprising instructions, which when executed by a server device in communication with a sterilizer device, cause the sterilizer device to:
monitor temperature and humidity within the sterilizer device;
receive, in response to input from a user, information associated with an initiation of a sterilization cycle of the sterilizer device;
monitor duration of the sterilization cycle;
receive information associated with an end of a sterilization cycle of the sterilizer device;
determine whether a current humidity measurement is greater than a predefined threshold; and
control the heating element to an ON operating state when the current humidity measurement is greater than the predefined threshold.

10. The computer readable storage medium of claim 9, wherein the auxiliary device further comprises an accelerometer and wherein the one or more programs include instructions, which when executed by the electronic device with the display, cause the device to:
monitor output from the accelerometer;
monitor elapsed time without receiving an electrical response from the accelerometer based upon the monitored output; and
transition the auxiliary device to a LOW-POWER operating state when the monitored elapsed time is greater than a second predefined threshold.

11. The computer readable storage medium of claim 10, wherein the one or more programs include instructions, which when executed by the electronic device with the display, cause the device to:
determine a start time of the sterilization cycle based upon the monitored temperature within the sterilizer device, wherein the start time corresponds to a time when a discrete temperature change occurs greater than a second predefined threshold;
determine an end time of the sterilization cycle based upon the monitored temperature within the sterilizer device, wherein the end time corresponds to a time when monitored temperature change begins to decrease at a predefined rate; and
determine a time duration of the sterilization cycle based upon the start time and the end time.

12. The computer readable storage medium of claim 11, wherein the one or more programs include instructions, which when executed by the electronic device with the display, cause the device to:
  transitioning the auxiliary device to a NORMAL operating state when output is monitored from the accelerometer;
  transmitting the duration of the sterilization cycle and information associated with the monitored temperature and the current humidity measurements to a server subsequent to transitioning to the NORMAL operating state.

13. The computer readable storage medium of claim 12, wherein the LOW-POWER operating state comprises transitioning the wireless transceiver of the auxiliary device to an OFF operating state.

14. The computer readable storage medium of claim 9, wherein the determining whether a current humidity measurement is above a predefined threshold is executed subsequent to the sterilization cycle.

15. The computer readable storage medium of claim 9, wherein the one or more programs include instructions, which when executed by the electronic device with the display, cause the device to:
  transmit the duration of the sterilization cycle and information associated with the monitored temperature and the current humidity measurements to a server.

16. The computer readable storage medium of claim 9, wherein the auxiliary device further comprises a fan and wherein the method further comprises controlling a fan to an ON operating state when the current humidity measurement is above the predefined threshold.

17. Method for controlling an environment within a sterilizer device, the method comprising:
  equipping an interior space of the sterilizer device with a removable device having a temperature sensor, a humidity sensor, a fan, a heating element, an accelerometer, and a wireless transceiver configured to communicate sensor readings;
  monitoring temperature and humidity within the sterilizer device using the removable device and transmitting the monitored temperature and humidity to a computing server;
  receiving, by the sterilization device, information associated with an initiation of a sterilization cycle of the sterilizer device, in response to input from a user;
  monitoring duration of the sterilization cycle using the removeable device;
  receiving, by the sterilization device, information associated with an end of a sterilization cycle of the sterilizer device;
  determining, by the removeable device, whether a current humidity measurement is greater than a first predefined threshold;
  controlling the heating element and the fan to an ON operating state when the current humidity measurement is greater than the first predefined threshold; and
  controlling the heating element and the fan to an OFF operating state when the current humidity measurement is less than a second predefined threshold.

18. The method of claim 17, further comprising:
  monitoring output from the accelerometer;
  monitoring elapsed time without receiving an electrical response from the accelerometer based upon the monitored output; and
  transitioning the auxiliary device to a LOW-POWER operating state when the monitored elapsed time is greater than a second predefined threshold wherein the LOW-POWER operating state comprises transitioning the wireless transceiver of the auxiliary device to an OFF operating state.

19. The method of claim 18, further comprising:
  transitioning the auxiliary device to a NORMAL operating state when output is monitored from the accelerometer; and
  transmitting the duration of the sterilization cycle and information associated with the monitored temperature and the current humidity measurements to a server subsequent to transitioning to the NORMAL operating state.

20. The method of claim 19, further comprising:
  determining a start time of the sterilization cycle based upon the monitored temperature within the sterilizer device, wherein the start time corresponds to a time when a discrete temperature change occurs greater than a second predefined threshold;
  determining an end time of the sterilization cycle based upon the monitored temperature within the sterilizer device, wherein the end time corresponds to a time when monitored temperature change begins to decrease at a predefined rate; and
  determining a time duration of the sterilization cycle based upon the start time and the end time.

* * * * *